United States Patent [19]

Triscott et al.

[11] Patent Number: 5,071,745
[45] Date of Patent: Dec. 10, 1991

[54] FIBRINOLYTIC ASSAY

[75] Inventors: Mark X. Triscott; George J. Doellgast, both of Winston-Salem, N.C.

[73] Assignee: Elcatech, Inc., Winston-Salem, N.C.

[21] Appl. No.: 284,299

[22] Filed: Dec. 14, 1988

[51] Int. Cl.$^5$ .................... G01N 33/573; C12Q 1/56; C12N 9/99

[52] U.S. Cl. ..................................... 435/7.4; 435/13; 435/7.71; 435/184

[58] Field of Search ...................... 435/13, 7, 28, 174, 435/180, 184, 188, 212–217, 7.4, 7.71

[56] References Cited

U.S. PATENT DOCUMENTS

| | | | |
|---|---|---|---|
| 3,778,352 | 12/1973 | Bishop et al. | 435/13 |
| 3,960,669 | 6/1976 | Innerfield | 435/13 |
| 4,011,142 | 3/1977 | Jacobi | 435/13 |
| 4,046,635 | 9/1977 | Moroz | 435/13 |
| 4,216,291 | 8/1980 | Collen | 435/7.25 |
| 4,463,090 | 7/1984 | Harris | 435/7.7 |
| 4,668,621 | 5/1987 | Doellgast | 435/13 |

FOREIGN PATENT DOCUMENTS 8606489 4/1985 World Int. Prop. O.

OTHER PUBLICATIONS

Mihama, Hisaharu, Quantitative determination of blood plasmin, Chemical Abstracts 102:92131u, 1985.
G. A. Beard et al., "Ulrasensitive Enzyme Linked Coagulator Assay (ELCA) of Factor V/Va", *J. Cell Biology* 107:828A (1988).

*Primary Examiner*—Esther L. Kepplinger
*Assistant Examiner*—Donna C. Wortman
*Attorney, Agent, or Firm*—Richard L. Neeley

[57] ABSTRACT

Assays and reagents for the determination of factors involved in fibrinolysis, wherein the assays involve the measurement of detectably labelled fibrin products which are released after digestion of a labelled fibrin complex prepared by adding soluble fibrinogen to solid-phase fibrinogen in the presence of thrombin, at least one of the fibrinogens being labelled. The label is preferably an enzyme label.

10 Claims, 7 Drawing Sheets

FIBRINOLYTIC ASSAY

BACKGROUND OF THE INVENTION

1. Field of the Invention

This invention is directed generally to assays involving blood clotting and clot removal and more particularly to assays for fibrinolytic activity.

2. Description of the Background

Fibrinolysis is the mechanism by which thrombin-generated fibrin clots are removed. The major components of the fibrinolytic system are plasminogen, plasminogen activators and inhibitors, and plasmin inhibitors. Plasminogen is the proenzyme in plasma, which upon conversion to its active form, plasmin, is considered primarily responsible for the digestion of fibrin clots.

Methods in this area may be broadly divided into bioassays for plasmin activity and immunoassays for the presence of various antigenic forms of tissue plasminogen activator (t-PA) or other component antigens of the fibrinolysis system. The purification and subsequent cloning of t-PA has allowed standardization of the inoculum for antibody preparations, but the diverse epitopes against which monoclonal antibodies have been raised make standardization of immunoassays using these reagents very difficult. The bioassay approach in which plasmin is measured is also subject to variation in that a number of different substrates are used, influencing the plasmin potency estimates.

For example, one bioassay method based on the lysis of fibrin creates a fibrin gel in a Petri dish through the addition of thrombin to fibrinogen. Then either purified fibrinolytic system components or plasma is added to the surface of the matrix, and the diameter of the zone of lysis is measured after 18 to 20 hours. This method is relatively slow, is not particularly accurate, and does not distinguish between intrinsic and extrinsic activators.

The bioassay method most often described in the literature is the chromogenic assay technique. In this technique a p-nitroaniline-linked tripeptide specific for the protease of interest is hydrolyzed, releasing the p-nitroaniline and resulting in a color change which can be followed spectrophotometrically. When this technique is applied to t-PA detection, however, a fibrin substitute is also needed to induce t-PA binding and consequent activity enhancement.

Immunological assays for components of the fibrinolytic system are generally applications of the normal ELISA or radiometric immunoassays. These systems fail to give an accurate measure of the activity of the system in vivo. Recently, bioimmunoassays have been developed which combine the immobilization features of the immunoassay approach with the functional aspects of the chromogenic assays. These bioassays do not utilize fibrin as the substrate or as a t-PA activity enhancer.

Recombinant t-PA offers a promising approach to coronary thrombolysis in patients with acute myocardial infarction due to coronary thrombosis. With the use of t-PA to achieve specific thrombolysis, assay systems for all aspects of the fibrinolytic system which are standardized, simplified, and readily available are needed. There is, therefore, a significant need for providing rapid and efficient assays which allow for high sensitivity, rapidity, and which are capable of automation for detecting a wide variety of factors of interest.

SUMMARY OF THE INVENTION

Methods and compositions are provided for detecting and measuring factors involved in the fibrinolytic system by measuring labelled fibrin products which are released after digestion of an enzyme-labelled fibrin complex. The labelled fibrin complex is formed by the action of thrombin on fibrinogen bound to a solid substrate in the presence of a liquid-phase fibrinogen. One or both of the fibrinogen phases is enzyme labelled. The factors detected by the method include enzymes, enzyme activators and inhibitors, and other components involved directly or indirectly in fibrinolysis.

BRIEF DESCRIPTION OF THE DRAWINGS

The invention being now generally described, the same will be more clearly understood by reference to the following detailed description of the invention when considered together with the following figures, wherein.

DESCRIPTION OF SPECIFIC EMBODIMENTS

Figure 1:
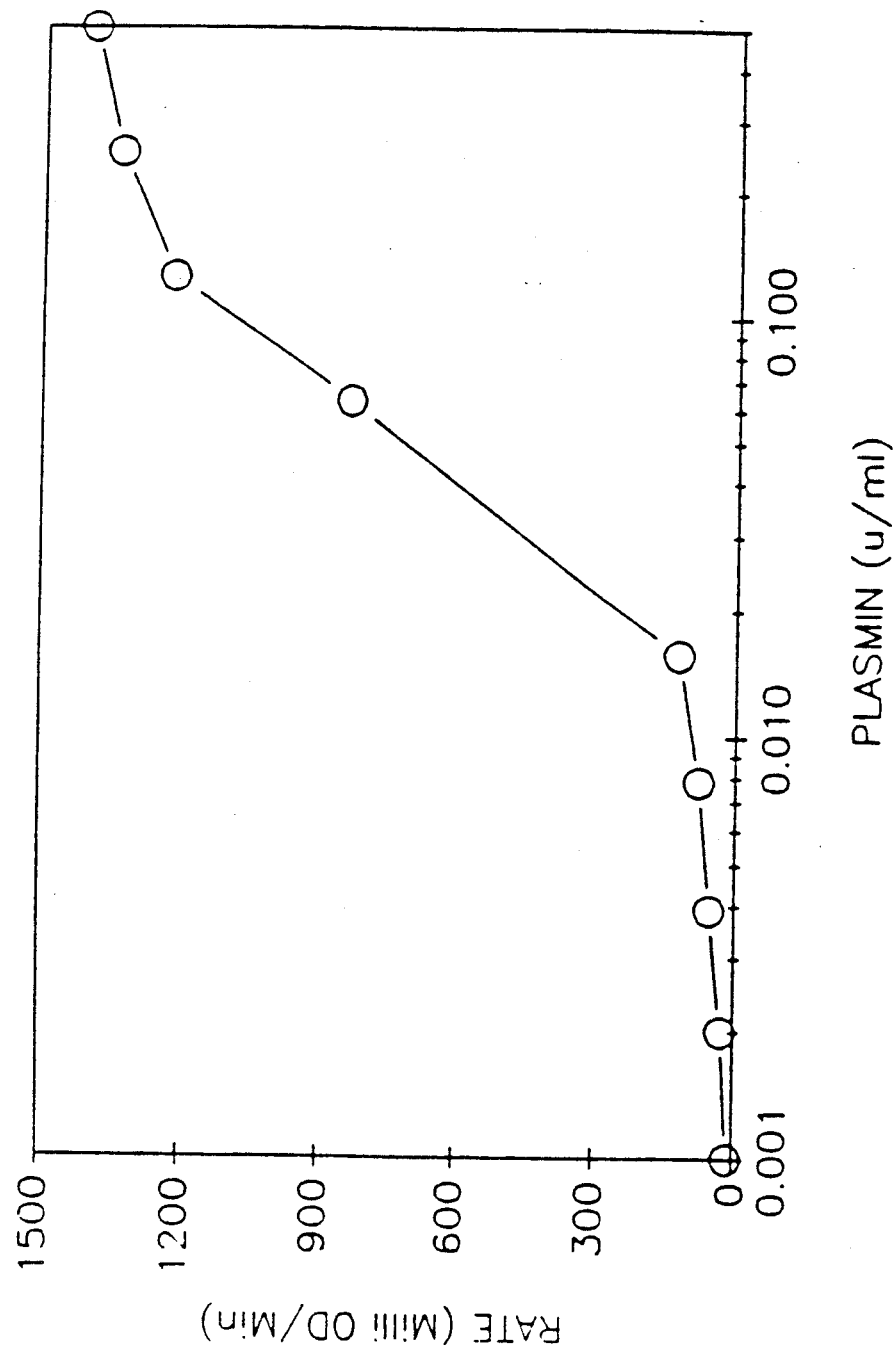
FIG. 1 is a graph giving representative data from a determination of the amount of plasmin in a mixture as measured by the quantitation of degradation products of enzyme-labelled fibrin produced from solid-phase/-liquid-phase, enzyme-labelled fibrinogen.

The subject method involves the use of enzyme-labelled fibrin, attached to a solid support, as a substrate for fibrinolytic enzymes and therefore as a component of an assay system for factors involved in fibrinolysis. Fibrinolytic factors, for the purpose of the present invention, include any enzyme, activator, inhibitor, antiactivator, antiplasmin, antibody, pharmaceutical, or the like, which affects the breakdown of fibrin either directly or indirectly. Thus, the assay can be used to detect a wide variety of factors, from any source, involved in the breakup of blood clots.

The assay calls for the action of an unknown factor on labelled fibrin bound to a solid substrate. The fibrin matrix is formed by a solid-phase/liquid-phase method. That is, a solid substrate is coated with unlabelled or labelled fibrinogen for a time sufficient to allow passive coating of the substrate with the fibrinogen. After washing the solid substrate to remove any unbound fibrinogen, liquid-phase, labelled or unlabelled fibrinogen is then added along with thrombin to form a labelled fibrin matrix. At least one of the two fibrinogen phases, the liquid phase or the solid phase, must be labelled. However, both phases can be labelled if desired. The signal to noise ratio is higher when labelled liquid-phase fibrinogen is used with either labelled or unlabelled solid-phase fibrinogen. Rates are higher for the labelled/labelled combination than for the unlabelled solid-/labelled liquid combination. However, the latter combination has a lower background, and the advantage of higher rates and the labelled/labelled combination is lost because the labelled reagent is more difficult to obtain than the naturally occurring unlabelled variety. Further, there is no gain in sensitivity. However, the labelled/labelled combination does develop color more quickly in a color test where purely qualitative criteria are being used.

In any case, the resulting labelled fibrin matrix can then be used as a substrate for fibrinolytic factors. The activity of the factors can be accurately and easily quantitated by the amount of label released in the degradation products of fibrinogen or fibrin. Because of the use of a substrate that has distinct physical and biochemical features as a result of being prepared from both solid-phase fibrinogen and liquid-phase fibrinogen, the assay is sometimes referred to in this specification as a "solid-phase/liquid-phase assay," with the understanding that this is a reference to the manner of making the substrate rather than a description of the assay itself.

The label employed in the instant method may be any molecule which does not interfere with fibrinolysis and allows for detection. A wide variety of labels have found use, such as enzymes, radionuclides, fluorescers, chemiluminescers, enzyme substrates and cofactors, enzyme inhibitors, and the like. The labels may be bound directly or indirectly to the fibrinogen, where various bridging groups may be employed such as antibodies, hapten-receptors, e.g., biotin-avidin, polynucleotides, or the like. Numerous patents have issued describing the use of these various materials, the following being illustrative of the group: U.S. Patent Nos. RE 29,169; RE 29,955; 3,654,090; 3,690,834; 3,817,837; 3,867,517; 3,935,074; 3,975,511; 3,996,345; and 4,020,151. The pH and buffer formulations used for the deposition of fibrin by thrombin are compatible with fluorescent and chemiluminescent labels so that these materials are easier to use as labels.

The preferred enzyme label for purposes of the instant method is peroxidase. When a peroxidase label is used, the assay is rapid, sensitive, and stable. For example, when horseradish peroxidase is used with the $H_2O_2$-tetramethylbenzidine substrate indicator, results are detected by color production within two minutes. Further, peroxidase-labelled fibrinogen and fibrin have shelf lives of greater than one year at $-20°$ C.

An alternative enzyme label that is particularly useful for some circumstances is urease. When urease is the label, the buffers used for an enzyme-linked fibrinolytic assay (ELFA) do not allow urease to be measured by the standard pH-change method. However, the enzyme is useful if some surface-bound urease-fibrin is removed by plasmin and decrease in fibrin-related activity that remains after the removal is measured This is a different technique from that described elsewhere in this application but has the advantage of not requiring transfer of solution so that it is particularly practical for diagnostic kit use. The general approach does not require the use of urease-fibrin but can be used with other enzymes, if desired.

When a urease label is used with a substrate solution containing urea and bromocresol purple, the reaction can be detected by a marked color change in two minutes. The shelf life of the label is comparable to that of peroxidase conjugates.

The present invention offers several advantages over current methods employed for quantitating fibrinolytic blood factors. A major advantage is the ability to use nonradioactive labels. Nonradioactive labels require no special handling techniques and do not present the problems of stability and proper disposal associated with radiochemicals. For the purposes of the present invention, an enzyme label, such as peroxidase, is preferred. An assay utilizing peroxidase has added advantages of being rapid, sensitive, stable, and cost effective when compared to conventional methods.

Figure 5:
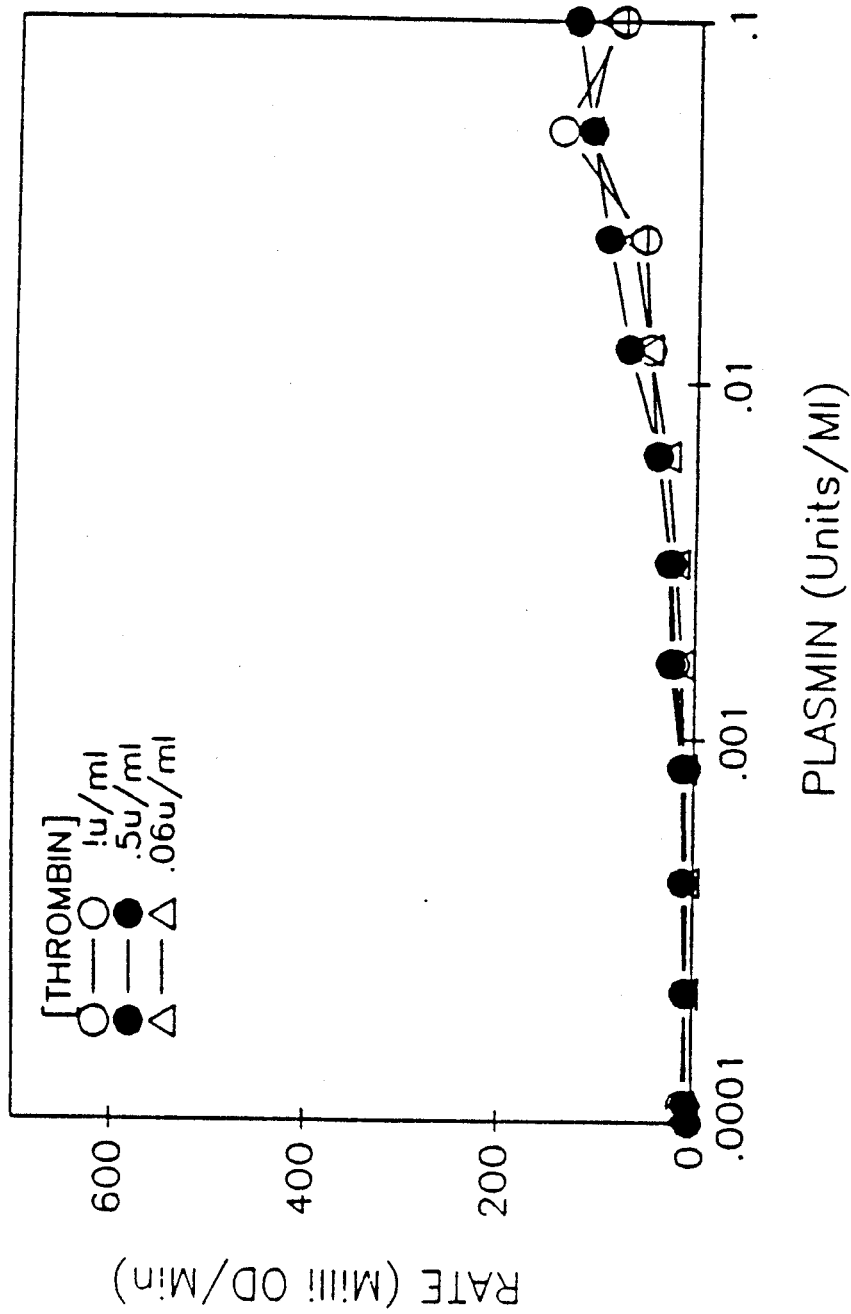
FIG. 5 is a graph showing the release of label by various levels of plasmin for solid-phase-prepared, peroxidase-labelled fibrin.
Figure 6:
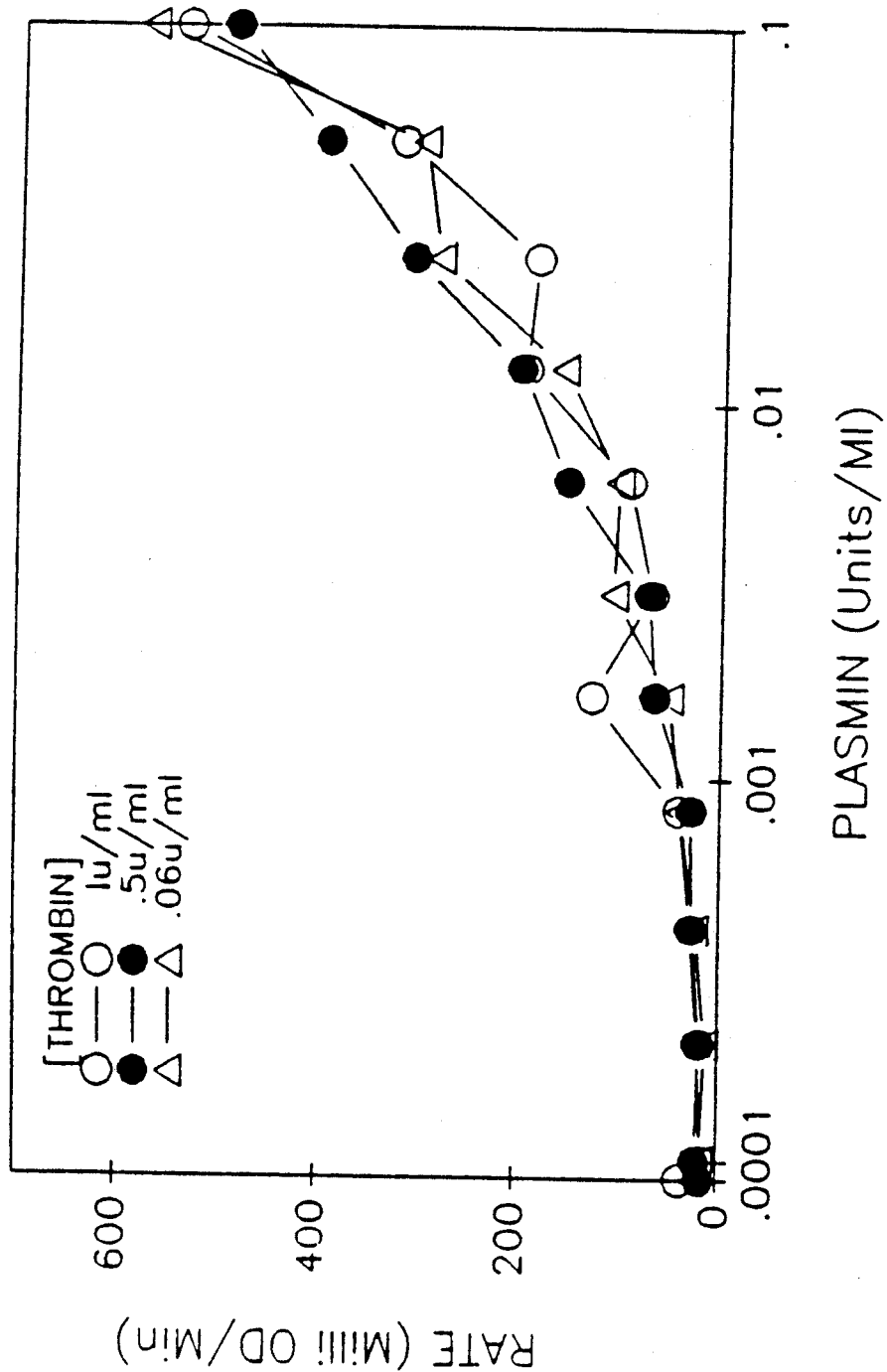
FIG. 6 is a graph showing the release of label by various levels of plasmin for solid-phase/liquid-phase-prepared, peroxidase-labelled fibrin.

The substrate fibrin that is produced by a solid-phase/liquid-phase method has a number of other properties that are also not available from solid-phase fibrins that have been previously produced. The mere substitution of nonradioactive enzyme labels for radioactive labels in conventional solid-phase techniques for producing fibrin does not produce a workable assay (see FIGS. 5, 6, and 7 and the discussion of the data reported in them, which follows). It is necessary to add fibrinogen in the liquid phase with thrombin to obtain a matrix suitable for the measurement of plasmin when an enzyme label is used. Preparation of the labelled substrate is described in detail below.

Further, the fibrin matrix produced as described here is ideal for all types of fibrinolytic assays. A major advantage over currently available commercial kits is that a natural substrate is being used for the fibrinolytic system components, rather than a smaller chromogenic substrate which may not be susceptible to natural fibrinolytic inhibitors. For example, t-PA-mediated activation of plasminogen is enhanced in the presence of fibrin, and fibrin is also the natural substrate for the end product of the activation, namely plasmin. Thus, the activation that occurs in the presence of the natural-like substrate of the invention gives a much more accurate representation of t-PA-mediated activation than that which occurs with the smaller chromogenic substrates used in other methods.

An assay of the invention also provides a much more rapid quantitation of fibrinolytic factors than is currently available, with comparable or increased sensitivity. This could prove to be especially useful in applying the assay for thrombolytic-therapy monitoring, as the time frame for current assays is considered clinically unacceptable. A corollary of this improvement is that inhibitor assays for components of this system will also be more sensitive and quicker.

The assay method involves the use of labelled fibrin produced from solid-phase/liquid-phase, labelled fibrinogen as a substrate for plasmin. As plasmin is generated or inhibited as the end product of all fibrinolytic events, its measurement is central to any assay technique of the invention. Thus, except when the assay is for plasmin, plasminogen is included in the reaction mixture. However, the assay can be varied to analyze for other components of the fibrinolytic system by providing various combinations of the components of the system, typically including all but the one component being assayed for. Accurate and sensitive measurements are achieved by detecting and quantitating the amount of label released from the fibrin matrix in the presence of the assay components and the sample. This release of label from the substrate of the invention closely mimics the in vivo situation.

Assays for different components of the fibrinolytic system, often referred to as factors, will require different protocols and reagents depending upon where the factor of interest interacts in the fibrinolytic pathway. Common to all the protocols will be the labelled-fibrin substrate of the invention bound to a support.

Assays for plasmin will not require additional reagents for fibrinolysis, although other reagents could be added to ensure the presence of other fibrinolytic system components in adequate amounts. The mixture of added factors that would be supplied as reagents in assays for other system components could be presented as diluted plasmas deficient in the factor of interest or as mixtures of purified factors lacking the factor of interest necessary for fibrinolysis. Alternatively, the plasma levels of various fibrinolytic factors can be measured for diagnostic purposes by comparing patient plasma with pooled normal plasma or a set of known standards to detect abnormalities.

The subject assays can be performed either "directly" or "indirectly," where indirectly will involve a competitive or secondary interaction affecting the production of plasmin or plasmin activity, while directly intends that the factor of interest has a direct effect, either activation or inhibition, on production of plasmin or plasmin activity Although the exact physiological mechanism of activation of plasminogen in vivo is not clear, all plasminogen activation studied to date occurs through the cleavage of the Arg560-Val561 peptide bond in plasminogen. There are two different activation pathways, the intrinsic or humoral pathway and the extrinsic pathway. Direct assays can be designed to measure activators and inhibitors of either pathway. Where the assay is for an activator involved in the formation of plasmin from plasminogen, it is necessary to include plasminogen and other components which the activator requires to produce plasmin. Activators involved in the intrinsic pathway include factor XII, (Hageman factor), prekallikrein, and high molecular weight kininogen (contact activating factor). Extrinsic activators include urokinase, streptokinase, and t-PA. For the three major activators of the extrinsic pathway there is a more favorable kinetic constant towards the conversion of plasmin in the presence of fibrin or certain fibrinogen fragments. Thus, the use of a fibrin matrix as a substrate for the instant method is more indicative of the activation occurring in vivo.

Similarly, where the factor to be assayed inhibits a particular component of the fibrinolytic system, then that component would be included with additional components necessary for the cleavage of plasminogen to form plasmin. If the factor is an antiplasmin, plasmin or all the components necessary for its production are provided in the assay mixture. Antiplasmins include $\alpha_2$-antiplasmin, $\alpha_2$-macroglobulin, and $\alpha_1$-antitrypsin.

Indirect assays involving a competitive or secondary interaction on plasmin activity or production can be performed. Where the inhibitor acts on an activator which promotes plasmin formation, it is necessary to include the activator, plasminogen, and other components required for the production of plasmin. The inactivator $C_1$ appears specific for the intrinsic pathway by inhibiting activated factor XII. The anti-activator t-PA inhibitor 1 (PAI-1) is a fast-acting inhibitor of t-PA and is a well characterized inhibitor of the extrinsic pathway. Other known inhibitors which may affect both pathways include antithrombin III complexes, $\alpha_2$-macroglobulin, $\alpha_1$-antitrypsin, and $\alpha_2$-antiplasmin. Further, the subject method can be used to assay for factors which affect these inactivators/inhibitors. These factors may affect fibrinolysis as a result of complex formation between the factor and its complementary binding member. By complex formation is intended the noncovalent bonding of a ligand and its complementary receptor, where the ligand and receptor define a specific binding pair.

The following table presents various combinations of purified factors and plasma that can be used for the determination of different fibrinolytic system components.

| Assay of: | Purified System Components | Comments |
|---|---|---|
| Plasmin | Plasmin | Not present in normal plasma |
| Plasminogen | t-PA, Urokinase, Streptokinase | Use normal plasma or a standard for measurement |
| Plasminogen Activators (t-PA, urokinase, streptokinase) | Plasminogen | May need to inactivate anti-activators, use standards |
| Plasmin Inhibitors | Plasmin | Use normal plasma or standard for measurement |
| Anti-activators | Activator, Plasminogen | Use pooled plasma to determine normal levels |

The assay is not limited to known factors which are involved in fibrinolysis. Rather, any factor, biological or synthetic, which affects the hydrolysis of fibrin can be detected and measured by the instant method.

Pooled normal human plasma may be used as a standard for fibrinolytic factors, and plasmas suspected of having genetic deficiency or of being for other reason incompetent can be compared with this standard. It will also be possible to prepare mixtures of purified factors minus the factor of interest using in some cases an enzyme which can activate individual factors.

In most instances, the components of fibrinolysis will cross-activate between species, that is, a fibrinolytic activator/inhibitor from one species will provide activity for fibrinolytic components from another species. Thus, the factors from such diverse species as mouse, rabbit, rat, monkey, cow, human, or the like, may find use, where the factor or factors may be titrated with samples having known amounts of activity as to the various fibrinolytic factors and the utility of the particular species determined. Accordingly, it will not be necessary to use human, components in the subject assay for human factors, although this could prove to be desirable.

As suggested earlier, not only can the subject technique be used with specific fibrinolytic factors, but also with naturally occurring or synthetic materials which may activate or inhibit one or more of the factors. Thus, one can use the subject methodology for measuring the presence of materials which modulate the activity of one or more of the fibrinolytic factors. An example of this modulation is the specific inhibition of $\alpha_2$-macroglobulin by monomethylamine hydrochloride, which allows $\alpha_2$-antiplasmin to be quantitated independent of the effect of $\alpha_2$-macroglobulin. This in turn allows the subject method to determine the inhibitory involvement of $\alpha_2$-macroglobulin by indirect assay.

The reagents would be mixed with a sample prior to or concurrently with contact of the resulting reaction solution with the labelled substrate of the invention. The sample would typically comprise whole blood or a fraction of whole blood, such as plasma. Additionally, the sample can comprise other biological fluids, such as urine, spinal fluid, and saliva, as well as other liquids or solids, such as medium from a cell culture that is producing a factor that influences fibrinolysis. For example, various blood fractions prepared for use in humans, such as platelet-rich fractions treated with various drugs or other synthetics which activate or inhibit fibrinolysis, could be used as a sample. Diluents, such as buffers, salt solutions, and any preservative and bulking agents as well as excess factors used in determination of specific inhibitor levels could also be present in the reaction solution.

The reaction solution would be mixed and incubated with the substrate for a time sufficient to effect fibrinolysis if the component being assayed for is present, thereby generating labelled fibrin products. The amount of labelled fibrin released into the reaction solution may be quantitated and used to determine the amount of factor present. Quantitation would be by any technique suitable for determining the amount of label, and therefore the amount of labelled fibrin fragments either in solution or remaining on the solid phase.

Where one is concerned with determining the activity of a particular component in a sample, for example, one would take a blood sample, dilute it to one or more (usually a plurality of) dilutions, and add it to a solution which will activate the plasminogen to plasmin. In this manner the contribution of the sample to the inhibition of plasmin will be negligibly small at the lowest dilution and measurable at the highest dilution. Thus the amount of plasminogen activated can be related to a pooled plasma solution or a standard, and the amount of inhibition displayed by the plasma can similarly be quantitated. Similarly, where one wishes to investigate an endogenous activator or inhibitor which may be present in a physiological sample, one would add dilutions of the plasma to a medium containing all of the factors, where the factors are present and the medium in sufficient amount to substantially overwhelm the contribution from the sample. Alternatively, where the particular material to be analyzed may be substantially concentrated and freed of other factors involved in the fibrinolysis, the concentrate may then be used and the amount of the various factors present in the medium may range from a substantial dilution of normal plasma to a concentrate.

The subject method provides a simple technique for the detection and quantitation of factors involved in fibrinolysis by measuring degradation products resulting from plasmin activity. Thus, the use of labelled support bound fibrin, formed by the solid phase-liquid phase method, and plasmin or plasminogen can be coupled to any system which allows for modulation of plasmin activity. A wide variety of systems have been developed that can find use with the subject detection system.

It may be necessary to determine the quantitation of complexes of activators and antiactivators or proteases and their specific inhibitors. There are a variety of methods available for these assays including the ELISA mode which can be coupled with the subject method. Alternatively, if a bioimmunoassay is required to determine residual activity of a factor within such a complex, this system may also be adapted to that purpose. One example is described by simultaneously precoating the solid phase with antiinhibitor or antiactivator antibody, then adding thrombin and labelled fibrinogen to produce the labelled fibrin matrix. The complex of interest will be immobilized on the antibody, extracting it from other inhibitors which would interfere with its activity. This allows the residual protease to readily act in the presence of its natural substrate, fibrin, thus giving a much more accurate representation of inhibition or activation.

The solid substrate or support utilized with the instant method can be present in a variety of ways, covalently bound to walls of microtiter wells, walls of capillaries, bound to particles (e.g., magnetic particles, latex, polysaccharides, or the like), or other surfaces. Of particular interest are microtiter plates, where the signal may be measured in a microtiter plate reader. These readers are now commercially available.

Those skilled in the art will realize that any increase in surface area of the solid phase will increase the available area for the deposition of labelled fibrin and thus increase the available surface and substrate for the action of plasmin. Thus, any technique that produces greater amounts of surface area allow the technique to produce quantitative results more rapidly.

As a first step in preparing the substrate, unlabelled or labelled fibrinogen is coated onto the surface of a solid substrate. The amount of fibrinogen will depend on the support material, its shape and surface, and the protocol to be employed in the assay for which the substrate is intended. To substantially reduce or eliminate nonspecific binding to the surface, the support may then be treated with an inert protein such as serum albumin. For example, a protein solution having about 1 to 20 mg/ml of protein will be contacted with a support for a time for the protein to bind to the surface, followed by washing and mild drying. Liquid-phase labelled or unlabelled fibrinogen is added in the range of about 1 $\mu$g/ml to about 10 $\mu$g/ml, preferably about 4 $\mu$g/ml in a gelatin (20 mg/ml) or other concentrated protein buffer, such as serum albumin. The protein appears to interfere with the activity of plasmin in the assay so that the protein is normally removed from the matrix during matrix formation. For example, gelatin in the thrombin part of matrix production is typically washed out after 40 minutes. If the gelatin is included in the plasmin assay, the signal is significantly reduced and the sensitivity and specificity of the assay suffer.

Thrombin is then added at levels of between 0.01 and 0.5 international units/ml, and this mixture is then incubated at room temperature for approximately 40 minutes. The support is then aspirated and washed to remove excess liquid and reagents. The support may be stored in this form, if desired. If the labelled fibrin-coated support is not to be used immediately after coating, the coating should be kept in a moderately humid environment to ensure its continued activity, such as by storing in contact with a buffered solution, which may contain a preservative.

Figure 7:
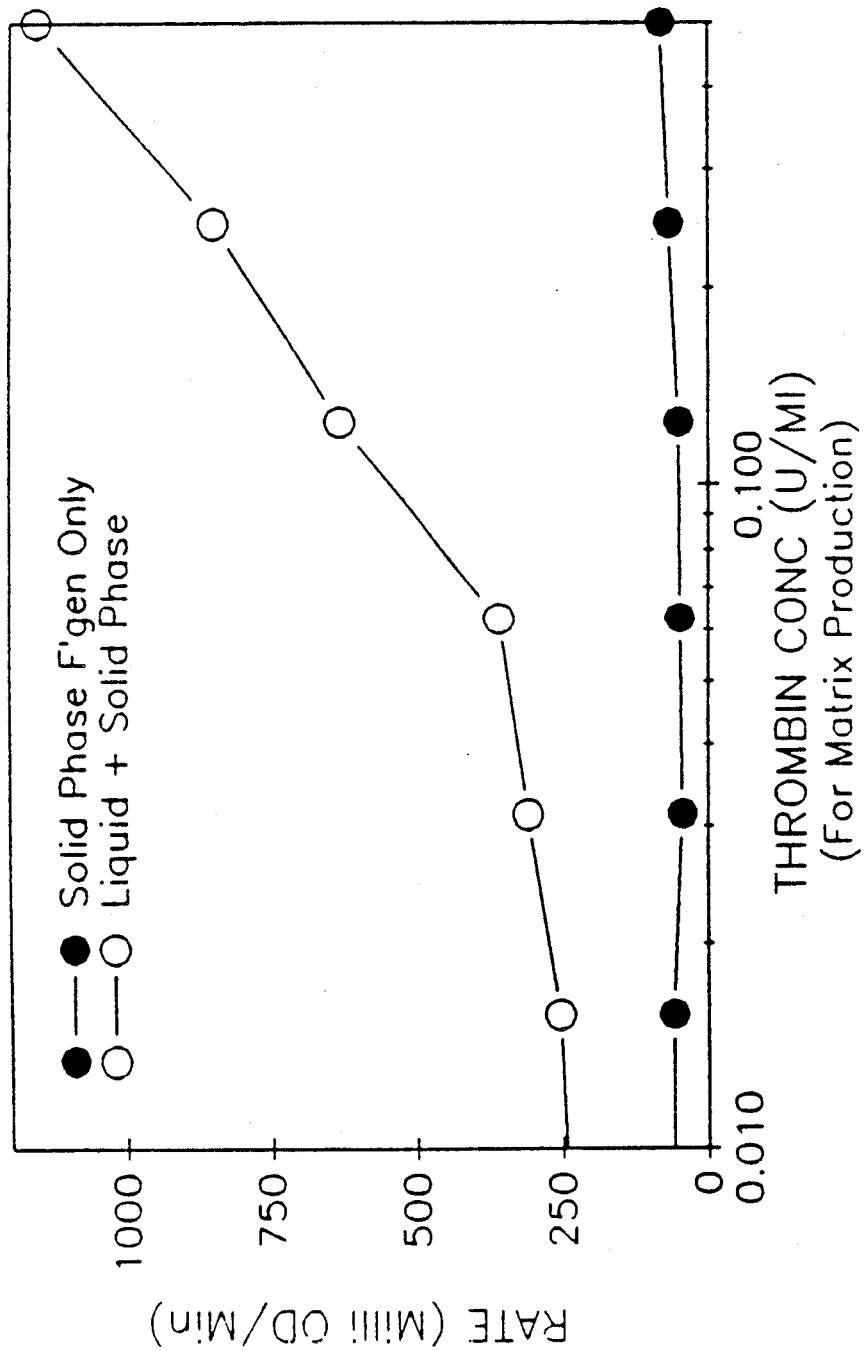
FIG. 7 is a graph showing data which indicates that the thrombin concentration used to generate the labelled fibrin matrix does not effect the solid phase only assay, whereas the solid-phase/liquid-phase assay shows enhanced signal with an increase in thrombin concentration.

The distinction of supplying liquid phase fibrinogen is crucial to obtaining a workable substrate and therefore a workable assay. Prior art techniques using passively bound labelled fibrinogen treated with thrombin to obtain a labelled fibrin matrix do not yield a matrix suitable for measurement of plasmin by the instant method. It is necessary to add fibrinogen, either labelled or unlabelled, in a liquid phase with thrombin to obtain a matrix suitable for measurement of plasmin. Results are presented showing the release of label by various levels of plasmin for a plate prepared by the instant method, solid-phase/liquid-phase method, and one prepared by supplying only solid-phase fibrinogen (see FIGS. 5 and 6 and their discussion below). In the solid-phase method there is virtually no differentiation, even at relatively high plasmin concentrations, while the solid-phase/liquid-phase-prepared plate shows a broad useful range for the detection of plasmin. Thus the instant method provides a more sensitive substrate matrix. Further experimentation has indicated that the sensitivity of the matrix can be enhanced even further by manipulating certain parameters. Illustrative data is presented which indicates that the thrombin concentration used to generate the labelled fibrin matrix does not affect the "solid phase only" assay, whereas the "solid-/liquid-phase" assay shows an enhanced signal with an increase in thrombin concentration (FIG. 7).

The assay utilizing solid-phase/liquid-phase supports may be carried out under mild temperature conditions, generally ranging from about 17° to about 37° C. The concentration of the various reagents will vary widely, depending upon the particular protocol, what is being measured, the concentration range of the factor of interest, whether a qualitative or quantitative determination is required, the time for the assay, and the like. Thus, the assay time may range from about 1 minute to 24 hours, more usually from about 1 minute to about 1 hour. The sensitivity of the assay permits the measurement of less than a picogram of t-PA in 4 hours. The media employed will normally be aqueous media, where small amounts of polar organic solvents may be included, usually less than 40 volume percent, more usually less than about 10 volume percent. The solutions will normally be buffered at a pH in the range from about 6 to 9, more usually from about 7 to 8.5. Various buffers may be employed such as phosphate, Tris, or the like, which do not already inhibit fibrinolysis.

The subject method can be used with any type of ligand, haptenic or antigenic, receptors, polynucleotides, or the like, by coupling an analyte of interest to a fibrinolytic factor and measuring differences in activity in the presence of sample containing different amounts of the analyte. Besides the fibrinolytic factors which have been previously described, drugs, hormones, enzymes, lymphokines, neurotransmitters, membrane proteins, regulatory proteins, growth factors, or the like, may all be of interest.

To aid in the use of the subject invention, kits can be provided containing the various reagents in preferred ratios so as to optimize the sensitivity of the method. For determination of blood factors, labelled fibrin coated containers, particularly microtiter plates and one or more factor-deficient plasmin substrates may be provided for the detection of different factors. The various reagents may be provided as lyophilized reagents, which may be reconstituted and provided in combination with buffers, stabilizers, inert proteins, such as serum albumins, or the like. For some applications, it may be desirable to lyophilize reagents in microtiter wells at concentrations appropriate for the assay. Where other than blood factors are involved, the kits may include the conjugate of the factor or a molecule which modulates the activity of plasmin. Other reagents may also be included in the kit, such as enzyme substrates and cofactors, to facilitate the use of an enzyme label. The technology can also be adapted to a flow system in which all of the necessary components for the assay are present in sequential solid phases. The sample is introduced to the solid phase, and either the released or the remaining enzyme-labelled fibrin matrix is measured Such a system can be successfully adapted for centrifugal analysis or other flow systems.

The following examples are offered by way of illustration and not by way of limitation.

EXPERIMENTAL

Example 1

Enzyme-Labelled Fibrinogen

Fibrinogen peroxidase conjugate was prepared by the method of Nakane and Kawaoi (*J. Histochem. Cytochem.* (1974) 22:1084) using 40 mg of horseradish peroxidase and 300 mg of human fibrinogen. The molar ratio of peroxidase to fibrinogen in the final product was 0.39. This was diluted with unlabelled fibrinogen to a concentration of 0.72 mg/ml of fibrinogen with the molar ratio of 0.12 moles of peroxidase per mole of fibrinogen, stored in 50% glycerol at $-20°$ C.

Example 2

Enzyme-Labelled Solid Phase Fibrin

A polystyrene microtiter plate was passively coated with peroxidase-labelled fibrinogen as set forth in Example 1 in a low ionic strength TRIS buffer at room temperature for approximately 1 hour. This plate can be stored at 4° C. for a period of weeks. The plate was aspirated and washed, and liquid-phase, peroxidase-labelled fibrinogen was then added in concentration in the range of 4 $\mu$g/ml in a 20 mg/ml gelatin (bovine skin - 60 bloom) Tris buffer containing 2 mM ethylenediaminetetraacetic acid (EDTA; pH 7.8–8.2). Thrombin was then added in the same buffer at levels of between 0.01 and 0.5 international units/ml, and this mixture was incubated at room temperature for approximately 40 minutes. The plate was then aspirated and washed.

The fibrin matrix was ready to be used as a substrate for any plasmin-generating substrate mixture. The amount of enzyme-labelled fibrin released into the plasmin-generating substrate mixture may be quantitated and used to determine the amount of plasmin generated. Representative data from such a quantitation is shown in FIG. 1 for the addition of a plurality of dilutions of a standardized preparation of plasmin. Standardization was carried out using CTA (Committee on Thrombolytic Agents) units. Dilutions were carried out in Tris-EDTA buffer and added in 50 $\mu$l aliquots to 50 $\mu$l of buffer previously dispensed into all wells of the microtiter plate containing the labelled fibrin matrix. The concentrations in FIG. 1 represent the concentrations for this further 2-fold dilution. This further dilution is necessary to enable the removal of exactly 50 $\mu$l for quantitation. Measurement of released peroxidase-fibrin breakdown products was achieved by transferring 50 $\mu$l of solution from the microtiter plate to the corresponding well in a fresh plate. After this transfer, 150 $\mu$l of horseradish peroxidase substrate (0.06% hydrogen peroxide and 20% ethanol with 1 mM tetramethylbenzidine and 0.16 M Tris citrate buffer at pH 5.15) was added to the transferred solution, and the resulting color change was monitored by spectrophotometric methods at a wavelength of 650 nm. The units of readings in FIG. 1 represent the results of a regression analysis of the change in milli-optical-density units per unit of time (minutes). Machines are currently available which routinely and automatically calculate this data. End-point optical density readings can also be used.

Example 3

Activator Assays

Figure 2:
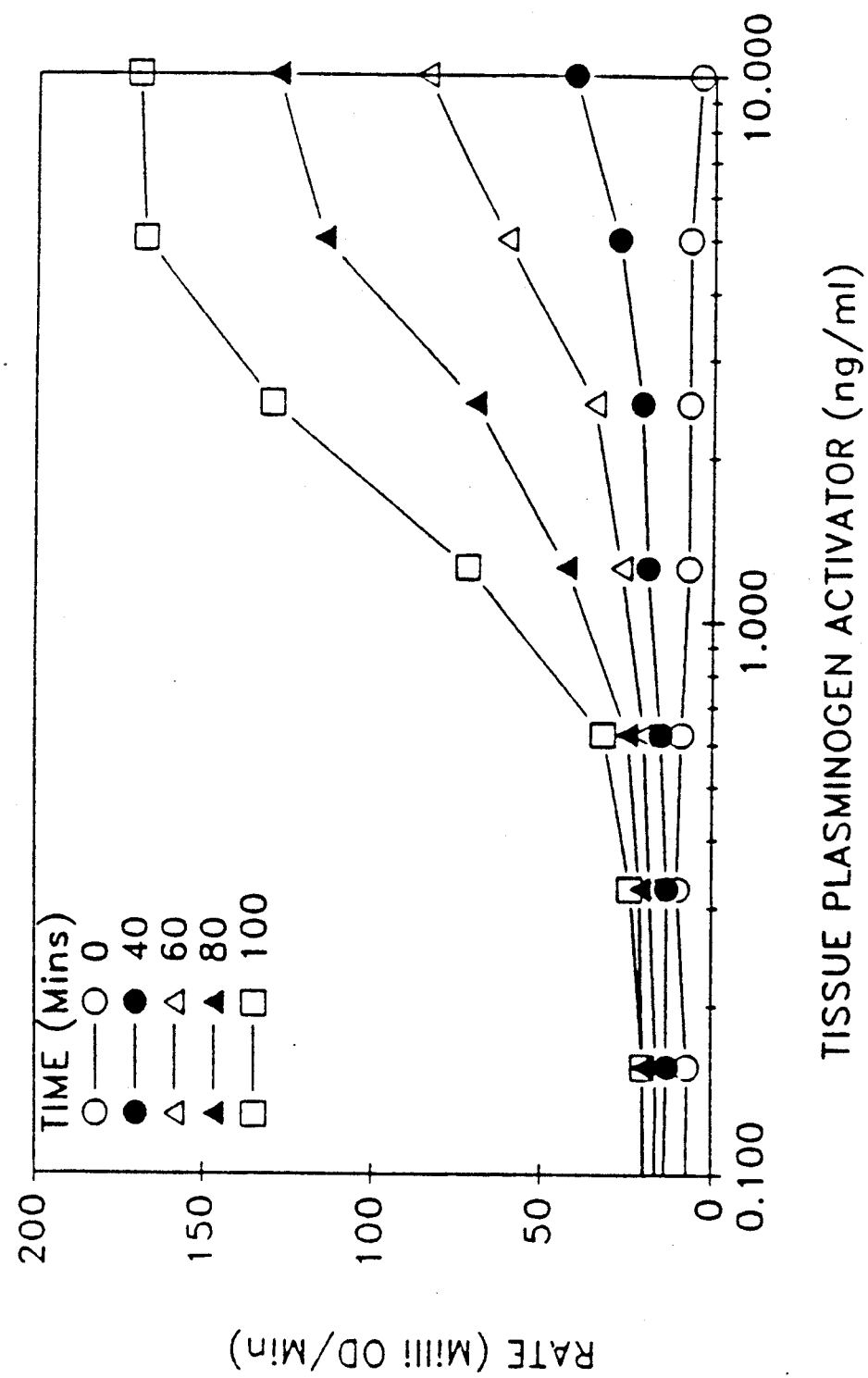
FIG. 2 is a graph giving results from the direct measurement of the plasminogen activator, t-PA.

Starting with a prelabelled plate prepared as described in Example 2, dilutions of tissue plasminogen activator in the range from 0.1 to 10.0 ng/ml were added. Plasminogen was then added in concentrations ranging from about 0.05 to 0.1 unit/ml to all the wells of the plate. The source of plasminogen was either purified plasminogen or plasminogen in plasma preparations. This reaction mixture was then incubated at room temperature for various times, after which 50 μl was removed, and the amount of peroxidase-label released was measured. The results of such an experiment allow the direct measurement of plasminogen activators including streptokinase and urokinase depending on the amount of plasmin present in plasminogen preparations, this assay can be carried out for at least 20 hours hours. Sensitivity after a 4-hour incubation is less than 1 pg/ml. Sample results are demonstrated in FIG. 2. By using such measurements as standards for the amount of activator present in an assay, it is possible to determine the amount of specific activator inhibitor present by comparing results after adding known amounts of activator in the presence and absence of specific inhibitor such as PAI-1 and PAI-2.

Example 4

Inhibitor Assays

Figure 3:
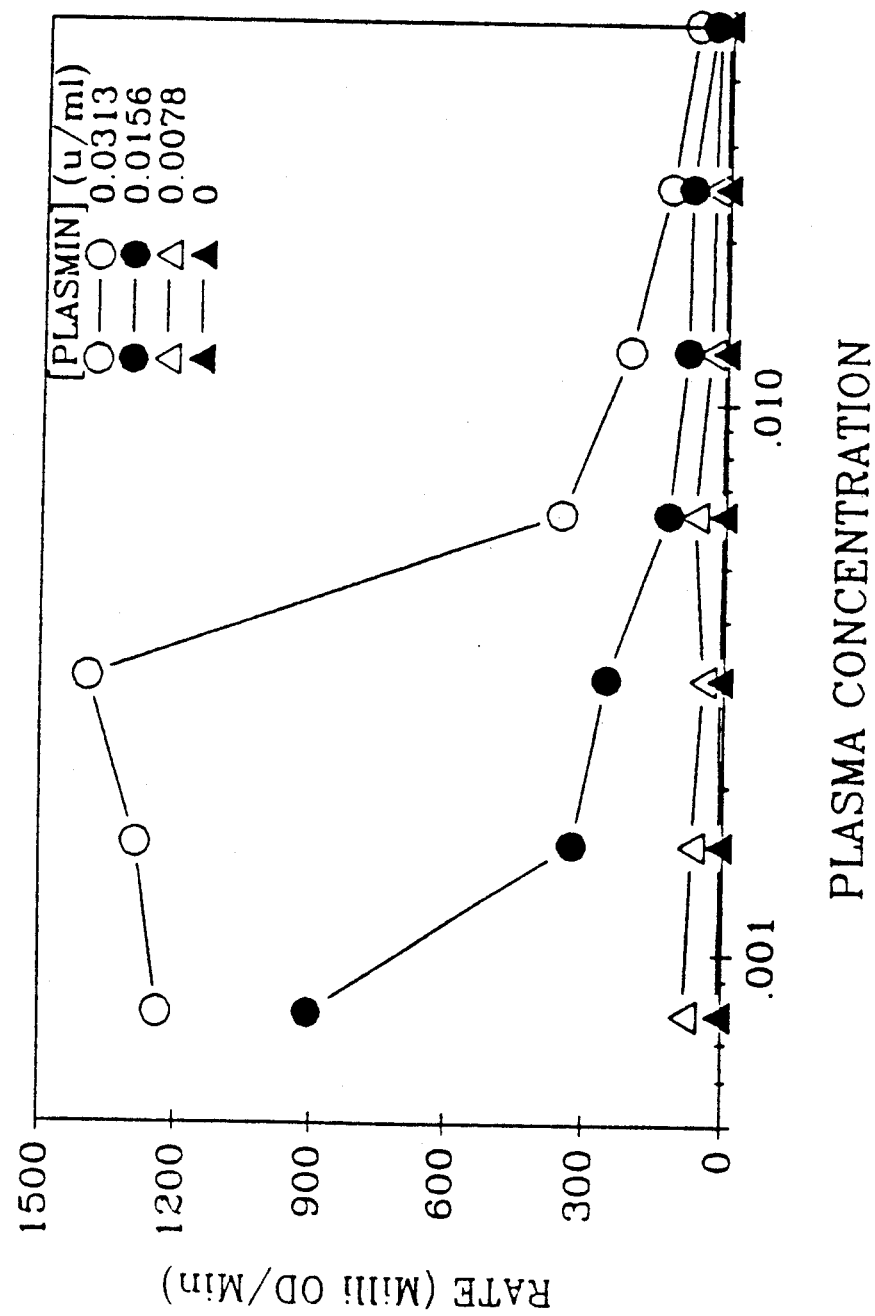
FIG. 3 is a graph giving results from the measurement of levels of inhibitors of the fibrinolytic system.

Using a prelabelled plate as prepared in Example 2, plasma at dilutions of between 1/50 and 1/1,000 was added and then plasmin at levels between 0.01 and 0.1 unit/ml was added. This reaction mixture was then incubated for between 30 and 60 minutes at room temperature and the amount of enzyme-label in the 50 μl aliquot of the reaction mixture was measured. This experiment allows the measurement of levels of inhibitors of the fibrinolytic system. Sample results are presented in FIG. 3.

Example 5

Immunoassay

Figure 4:
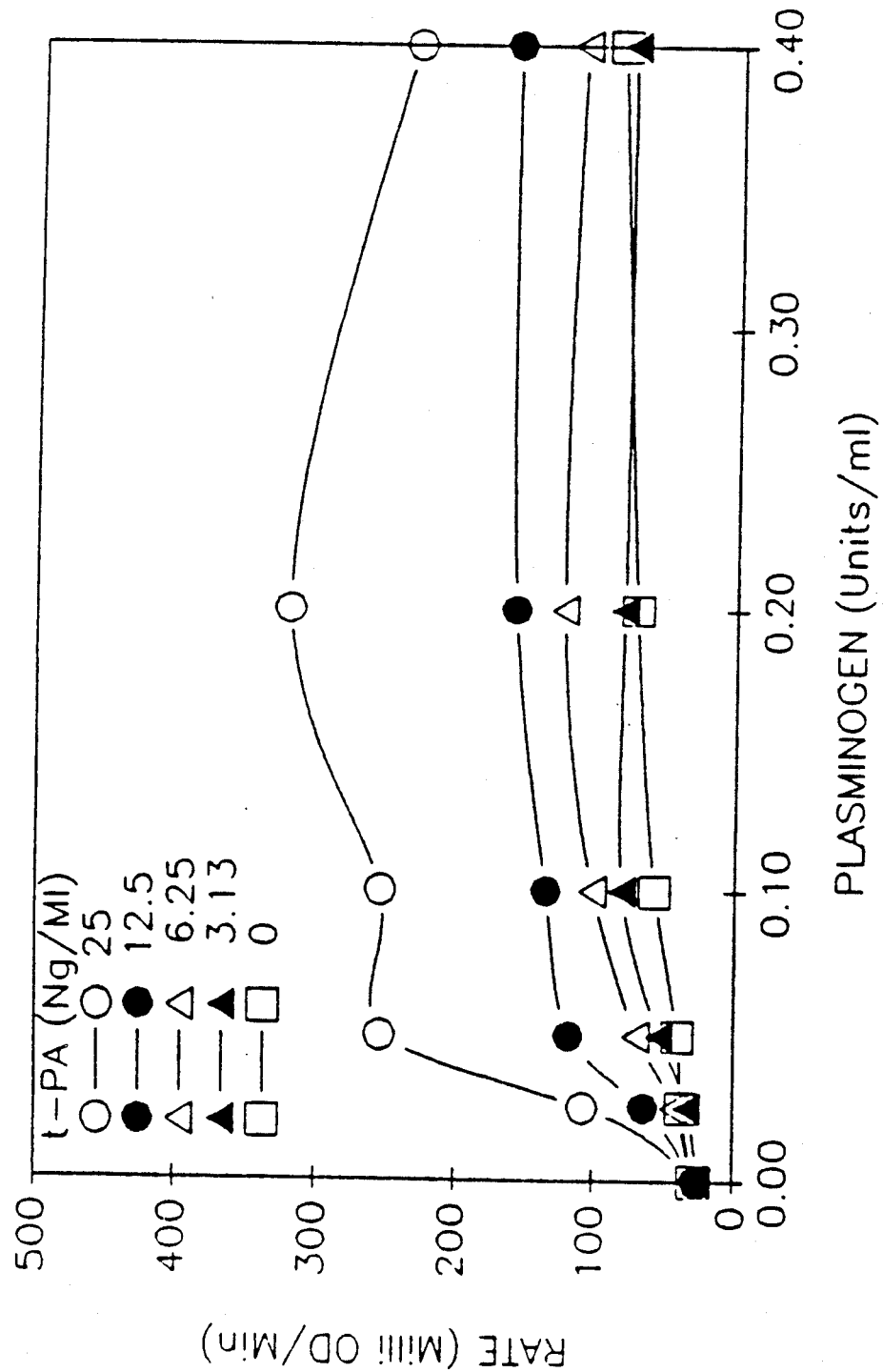
FIG. 4 is a graph giving results from an immunoassay for the detection of t-PA.

A fibrinogen coated plate was also passively coated with anti t-PA antibodies for approximately 1 hour at room temperature. A labelled fibrin matrix was then generated on the plate as described in Example 2. An unknown amount of t-PA and plasma was added, and the mixture was allowed to incubate for a further hour. The plate was then aspirated and washed, after which plasminogen was added. After incubation, the peroxidase label released in a 50 μl aliquot of the reaction mixture was measured. This method detected t-PA in the plasma. Further, by using purified t-PA in the binding step, then plasma in a short second step, the method could be used to detect specific t-PA inhibitors such as t-PAI-1. Representative results of this functional immunoassay method is presented in FIG. 4.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for detecting in a sample an analyte comprising a factor of or a factor which interacts with a human fibrinolytic system, comprising:
   1) contacting said sample with a detectably labelled fibrin substrate to form a reaction mixture, wherein said substrate is prepared prior to contact with said sample by coating a solid surface with fibrinogen and adding soluble fibrinogen and thrombin to said coated fibrinogen, wherein either said fibrinogen coated on said solid surface or said soluble fibrinogen is detectably labelled or both are detectably labelled, and wherein said reaction mixture further contains sufficient factors of said fibrinolytic system to cause fibrinolysis in the presence of said analyte, and
   2) detecting labelled fibrin products released into said reaction mixture after said contacting as a measure of the analyte.

2. A method as recited in claim 1, wherein said detecting comprises quantitative measurement of said factor in said sample.

3. A method as recited in claim 1, wherein said detectably labelled fibrinogen is labelled with an enzyme.

4. A method as recited in claim 3, wherein said enzyme label is peroxidase.

5. A method as recited in claim 1, wherein said factor is an activator of fibrinolysis and said mixture further contains plasminogen.

6. A method as recited in claim 5, wherein said factor is tissue plasminogen activator.

7. A method as recited in claim 1, wherein said sample is a whole-blood, plasma, or serum sample.

8. A method as recited in claim 1, wherein said factor is an inhibitor of fibrinolysis and said mixture further contains plasminogen.

9. A method as recited in claim 1, wherein said factor is an antiplasmin and said mixture further contains plasminogen.

10. A method as recited in claim 1, wherein said factor is plasminogen.

* * * * *